US007260979B2

(12) United States Patent
Matsuda et al.

(10) Patent No.: US 7,260,979 B2
(45) Date of Patent: Aug. 28, 2007

(54) OXYGEN SENSOR

(75) Inventors: Atsushi Matsuda, Gunma (JP); Nobuaki Sekiya, Gunma (JP); Motomichi Kambayashi, Gunma (JP)

(73) Assignee: Hitachi, Ltd., Tokyo (JP)

( * ) Notice: Subject to any disclaimer, the term of this patent is extended or adjusted under 35 U.S.C. 154(b) by 175 days.

(21) Appl. No.: 11/004,894

(22) Filed: Dec. 7, 2004

(65) Prior Publication Data
US 2005/0126261 A1 Jun. 16, 2005

(30) Foreign Application Priority Data
Dec. 15, 2003 (JP) ............................. 2003-416473
Jan. 23, 2004 (JP) ............................. 2004-015483
Feb. 25, 2004 (JP) ............................. 2004-049611

(51) Int. Cl.
*G01N 7/00* (2006.01)
(52) U.S. Cl. .................................................. 73/31.05
(58) Field of Classification Search ................. 73/31.05
See application file for complete search history.

(56) References Cited

U.S. PATENT DOCUMENTS

| 4,958,514 | A | * | 9/1990 | Takami et al. ............. 73/25.03 |
| 5,246,562 | A | * | 9/1993 | Weyl et al. ................. 204/424 |
| 5,423,972 | A | * | 6/1995 | Mann et al. ................ 204/424 |
| 5,546,787 | A | | 8/1996 | Haifele et al. |
| 5,922,938 | A | * | 7/1999 | Hafele ........................ 73/23.32 |
| 5,948,226 | A | * | 9/1999 | Sakawa et al. ............. 204/424 |
| 6,082,175 | A | * | 7/2000 | Yoshikawa et al. ......... 73/23.31 |
| 6,322,681 | B1 | * | 11/2001 | Weyl ........................... 204/424 |
| 6,383,353 | B1 | * | 5/2002 | Akatsuka et al. ........... 204/424 |
| 6,395,159 | B2 | * | 5/2002 | Matsuo et al. .............. 204/427 |
| 6,477,887 | B1 | * | 11/2002 | Ozawa et al. ............... 73/31.05 |
| 6,660,143 | B1 | * | 12/2003 | Akatsuka et al. ........... 204/424 |
| 6,682,639 | B2 | * | 1/2004 | Atsumi et al. .............. 204/428 |
| 6,688,157 | B2 | * | 2/2004 | Yamada et al. .............. 73/23.2 |
| 6,726,819 | B2 | * | 4/2004 | Atsumi et al. .............. 204/428 |
| 6,898,961 | B2 | * | 5/2005 | Yamada et al. ............. 73/31.05 |
| 2002/0138967 | A1 | | 10/2002 | Yasuo et al. |

FOREIGN PATENT DOCUMENTS

| EP | 0 624 790 A | 11/1994 |
| EP | 0 836 094 A | 4/1998 |
| JP | 2001-188060 A | 7/2001 |
| JP | 2001 349863 A | 12/2001 |
| JP | 2002 156352 A | 5/2002 |
| WO | WO 01/35087 A2 | 5/2001 |

* cited by examiner

*Primary Examiner*—Hezron Williams
*Assistant Examiner*—Rodney Frank
(74) *Attorney, Agent, or Firm*—Sughrue Mion, PLLC

(57) ABSTRACT

An oxygen sensor includes a sensor element, a holder having a hole through which the sensor element is arranged, a sealing positioning portion for sealing a clearance between the sensor element and the holder and positioning the sensor element in the holder and being filled with a ceramic powder, terminals arranged to be in contact with the sensor element and for taking an output from the sensor element, an insulator secured to the holder at a first end and for holding the terminals, a casing secured to the holder at the first end and for covering an outer periphery of the insulator, and a protector secured to the holder at a second end and for covering an outer periphery of a portion of the sensor element, the portion protruding from the second end of the holder.

15 Claims, 7 Drawing Sheets

OXYGEN SENSOR

BACKGROUND OF THE INVENTION

The present invention relates to an oxygen sensor arranged in the exhaust system of an internal combustion engine for a motor vehicle, for example, to sense the concentration of oxygen in exhaust gas.

Various oxygen sensors are available for general use. As disclosed in U.S. Pat. No. 6,477,887, an oxygen sensor comprises typically a sensor element for sensing an oxygen concentration and converting it to an electric signal, an element securing insulator having an element hole through which the sensor element is arranged, a sealing positioning portion for sealing a clearance between the element securing insulator and the sensor element by a glass sealant and positioning the sensor element in the element securing insulator, terminals arranged to be in press contact with respective contacts of the sensor element which protrude from the element securing insulator and for taking an output from the sensor element, a terminal holding insulator arranged on the top face of the element securing insulator and for holding the terminals, a holder arranged at the outer periphery of the element securing insulator and for holding the element securing insulator, a casing secured to the holder at a first end and for covering the outer periphery of the terminal holding insulator, and a protector secured to the holder at a second end and for covering the outer periphery of the sensor element protruding from the element securing insulator.

The oxygen sensor is secured to an exhaust pipe by engaging a thread of the holder with the exhaust pipe, and is disposed with its portion covered with the protector protruding into the exhaust pipe.

SUMMARY OF THE INVENTION

However, the above oxygen sensor is of the structure having two insulators, i.e. element securing insulator and terminal holding insulator, and thus needs additionally holder for holding the element securing insulator, raising a problem of increasing the number of parts and the overall length of the oxygen sensor.

It is, therefore, an object of the present invention to provide an oxygen sensor which allows a reduction in number of parts and overall length of the oxygen sensor.

Generally, the present invention provides an oxygen sensor, which comprises: a sensor element which senses an oxygen concentration and convert it to an electric signal; a holder having a hole through which the sensor element is arranged; a sealing positioning portion which seals a clearance between the sensor element and the holder and positions the sensor element in the holder, the sealing positioning portion being filled with a ceramic powder; terminals arranged to be in contact with the sensor element, the terminals taking an output from the sensor element; an insulator secured to the holder at a first end, the insulator holding the terminals; a casing secured to the holder at the first end, the casing covering an outer periphery of the insulator; and a protector secured to the holder at a second end, the protector covering an outer periphery of a portion of the sensor element, the portion protruding from the second end of the holder.

BRIEF DESCRIPTION OF THE DRAWINGS

The other objects and features of the present invention will become apparent from the following description with reference to the accompanying drawings, wherein.

DETAILED DESCRIPTION OF THE INVENTION

Figure 1:
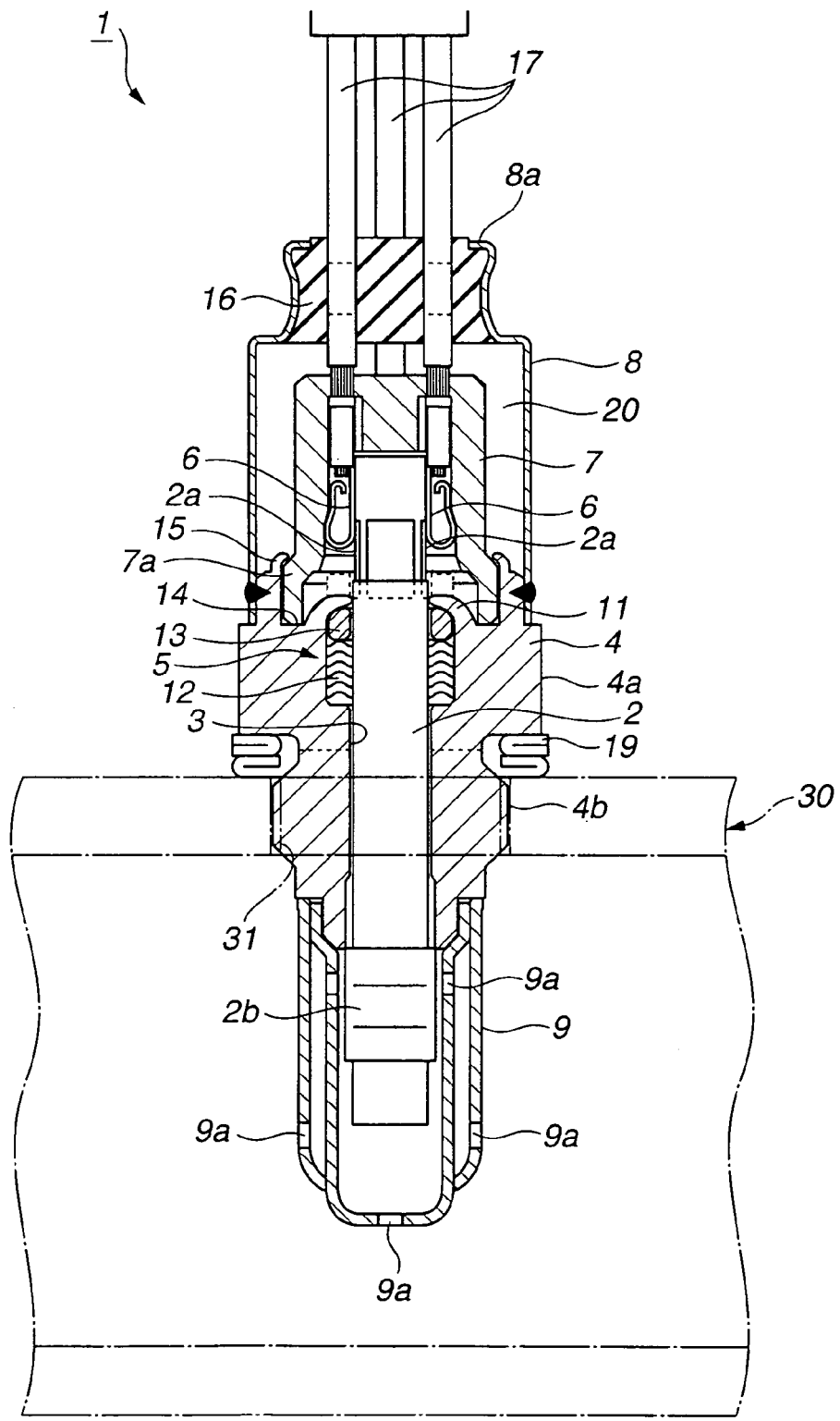
FIG. 1 is a sectional view showing a first embodiment of an oxygen sensor according to the present invention.

Referring to the drawings, a description will be made about preferred embodiments of an oxygen sensor according to the present invention.

Figure 2:
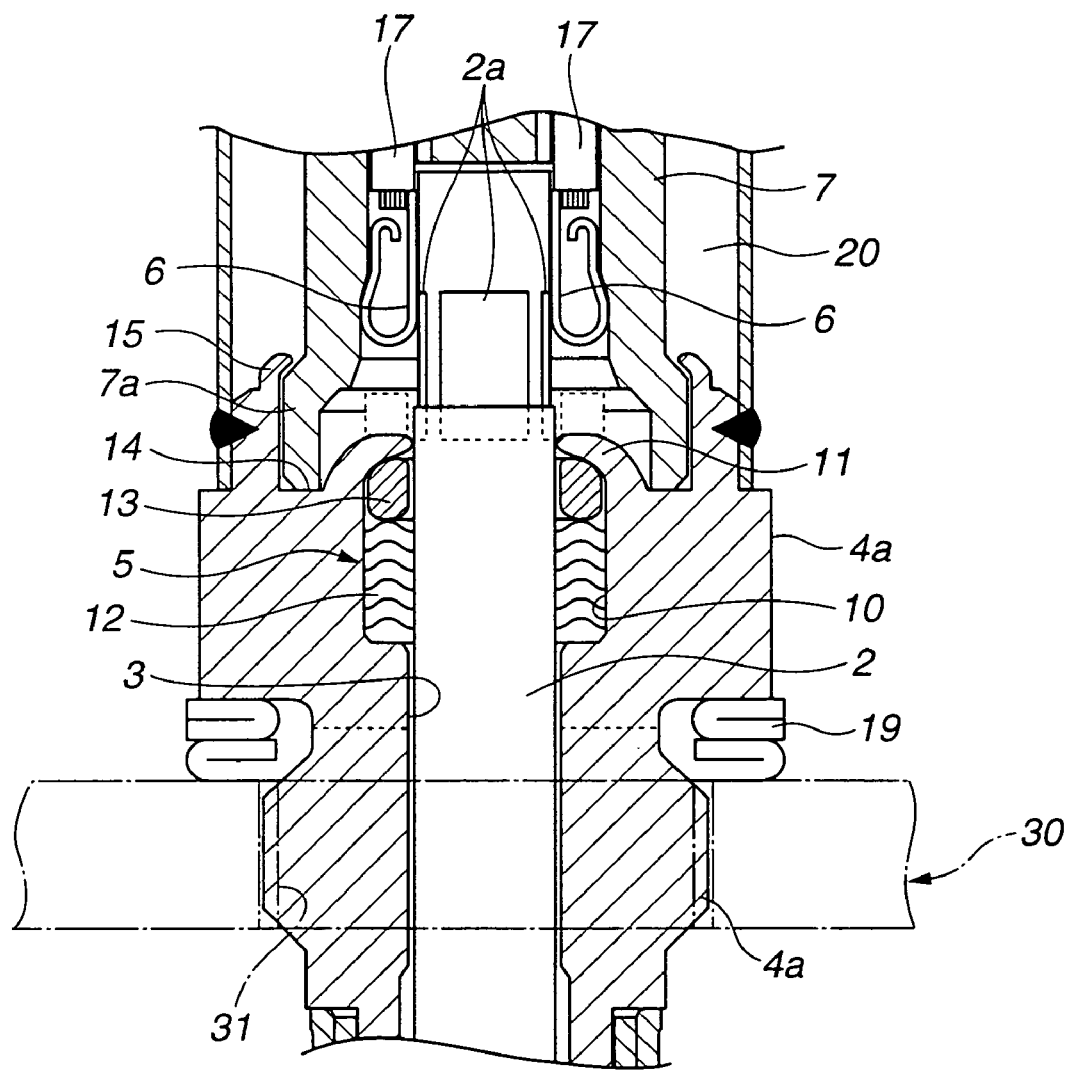
FIG. 2 is an enlarged fragmentary sectional view showing the oxygen sensor in FIG. 1.

Referring to FIGS. 1 and 2, there is shown first embodiment of the present invention. Referring to FIG. 1, an oxygen sensor 1 comprises a sensor element 2 for sensing an oxygen concentration and converting it to an electric signal, a holder 4 having an element hole 3 through which sensor element 2 is arranged, a sealing positioning portion 5 for sealing a clearance between holder 4 and sensor element 2 and positioning sensor element 2 in holder 4, terminals 6 arranged to be in press contact with respective contacts 2a of sensor element 2 which protrude upward from holder 4 and for taking an output from sensor element 2, a terminal holding insulator 7 secured to holder 4 at a first end and for holding terminals 6, a casing 8 secured to holder 4 at the first end and for covering the outer periphery of terminal holding insulator 7, and a protector 9 secured to holder 4 at a second end and for covering the outer periphery of sensor element 2 protruding from holder 4.

Sensor element 2 is shaped like a cylindrical rod, and includes contacts 2a at the top and an oxygen measuring portion 2b at the bottom.

Holder 4 includes at the top a hexagonal portion 4a presenting a hexagon when viewed from above. By engaging a tool with hexagonal portion 4a, a torque can readily be provided to holder 4. A thread 4b is formed with the outer periphery of the bottom of holder 4. A gasket 19 is interposed between hexagonal portion 4a and thread 4b of holder 4.

Referring to FIG. 2, sealing positioning portion 5 comprises a powder filling space 10 arranged at the overall outer periphery of element hole 3 and a caulking (first caulking) 11 arranged in the vicinity of powder filling space 10. A ceramic powder 12 and a resilient spacer 13 are accommodated in powder filling space 10. Spacer 13 is compressed by caulking 11 having caulked deformation to charge ceramic powder 12 in the compressed state, sealing a clearance between sensor element 2 and holder 4 and positioning sensor element 2 in holder 4. Ceramic powder 12 comprises un-sintered talc, and spacer 13 comprises a washer, for example.

Referring to FIG. 2, holder 4 is secured to terminal holding insulator 7 by arranging an insulator positioning groove 14 at an upper end of holder 4 and a caulking (second caulking) 15 at the outer periphery of insulator positioning groove 14, wherein a first-end-side large-diameter portion 7a of terminal holding insulator 7 is disposed in insulator positioning groove 14, and caulking 15 having caulked deformation is engaged with a step of large-diameter portion 7a.

Terminals 6 are shaped to provide a resiliency, and make contact with contacts 2a of sensor element 2 with the aid of their resiliency. A contact position of contacts 2a of sensor element 2 and terminals 6 is set just above the upper end face of holder 4.

Referring to FIG. 1, a sealing rubber 16 is arranged inside the top of casing 8, and a plurality of harnesses 17 are led outward therethrough. One ends of harnesses 17 are connected to terminals 6. Casing 8 includes a caulking 8a by which sealing rubber 16 is secured to casing 8 and through which the sealing quality is ensured between sealing rubber 16 and harnesses 17 and between sealing rubber 16 and casing 8.

Casing 8 is shaped cylindrically, and is secured to holder 4 by laser welding, for example, through which the sealing quality is ensured between casing 8 and holder 4. Casing 8 is sufficiently larger in contour than terminal holding insulator 7, which provides a void 20 between casing 8 and terminal holding insulator 7.

Protector 9 is shaped like a bottomed and double-structured cylinder, and has side walls through which small holes 9a for gas circulation are formed. Protector 9 is secured to holder 4 by laser welding, for example. Optionally, other fixing method such as spot welding or caulking can be adopted.

Oxygen sensor 1 is secured to an exhaust pipe 30 by engaging thread 4b of holder 4 in a threaded hole 31 of exhaust pipe 30, and is disposed with its portion covered with protector 9 protruding into exhaust pipe 30. The airtightness between oxygen sensor 1 and exhaust pipe 30 is ensured by gasket 19.

With the structure, when gas circulating through exhaust pipe 30 flows into oxygen sensor 1 through small holes 9a of protector 9, oxygen contained in gas enters oxygen measuring portion 2b of sensor element 2. Then, oxygen measuring portion 2b senses a concentration of oxygen contained in gas and converts it to an electric signal. This electric-signal information is output to the outside through terminals 6 and harnesses 17.

In the first embodiment, sensor element 2 is sealed and positioned in holder 4 by sealing positioning portion 5, allowing canceling of the element securing insulator which is required in the related art, resulting in a reduction in number of parts and overall length of oxygen sensor 1.

Further, in the first embodiment, sealing positioning portion 5 comprises powder filling space 10 arranged at the overall outer periphery of element hole 3 and caulking 11 arranged in the vicinity of powder filling space 10. Ceramic powder 12 and resilient spacer 13 are accommodated in powder filling space 10, and spacer 13 is compressed by caulking 11 having caulked deformation to charge ceramic powder 12 in the compressed state. Thus, sensor element 2 can surely be sealed and positioned by compressed ceramic powder 13.

Still further, in the first embodiment, holder 4 is secured to terminal holding insulator 7 by arranging insulator positioning groove 14 in holder 4 and caulking 15 at the outer periphery of insulator positioning groove 14, wherein the first end of terminal holding insulator 7 is disposed in insulator positioning groove 14, and caulking 15 having caulked deformation is engaged with terminal holding insulator 7. Therefore, even when terminal holding insulator 7 undergoes an external force due to pulling of harnesses 17 or the like, caulking 15 can bear this external force, resulting in sure fixing of terminal holding insulator 7 and holder 4.

Furthermore, in the first embodiment, sensor element 2 is shaped like a rod, allowing accurate detection of the oxygen concentration without being influenced by the orientation of sensor element 2, the direction of gas flow, and the like.

Further, in the first embodiment, void 20 is arranged between casing 8 and terminal holding insulator 7. Thus, sensor element 2 and terminals 6 are externally concealed double with casing 8 and terminal holding insulator 7, and are disposed therein through void 20 with excellent heat-insulation characteristics, resulting in enhanced durability in the high-temperature environment.

Still further, in the first embodiment, a contact position of contacts 2a of sensor element 2 and terminals 6 is set just above the upper end face of holder 4, allowing further reduction in overall length of oxygen sensor 1.

Figure 3:
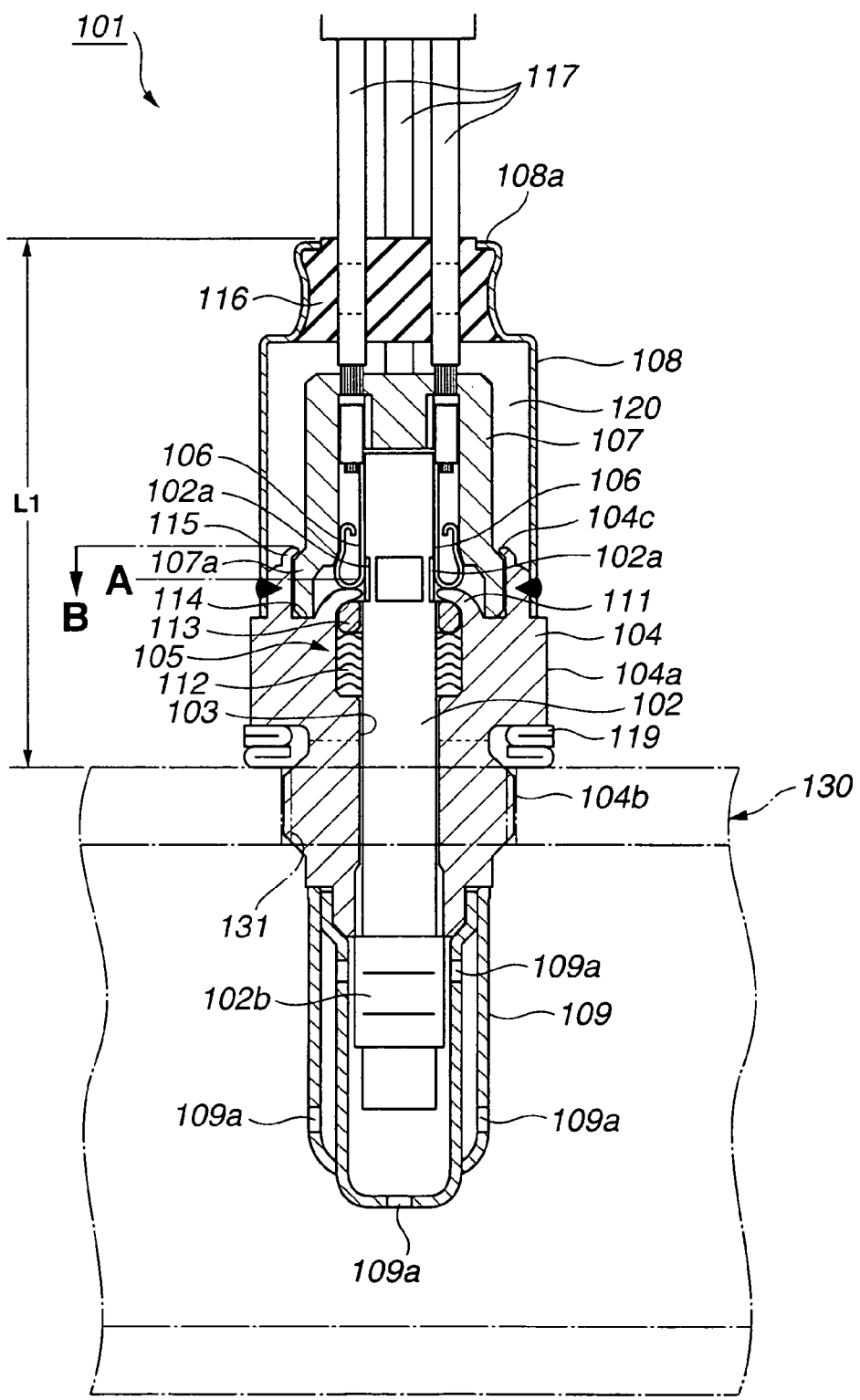
FIG. 3 is a view similar to FIG. 1, showing a second embodiment of the present invention.
Figure 4:
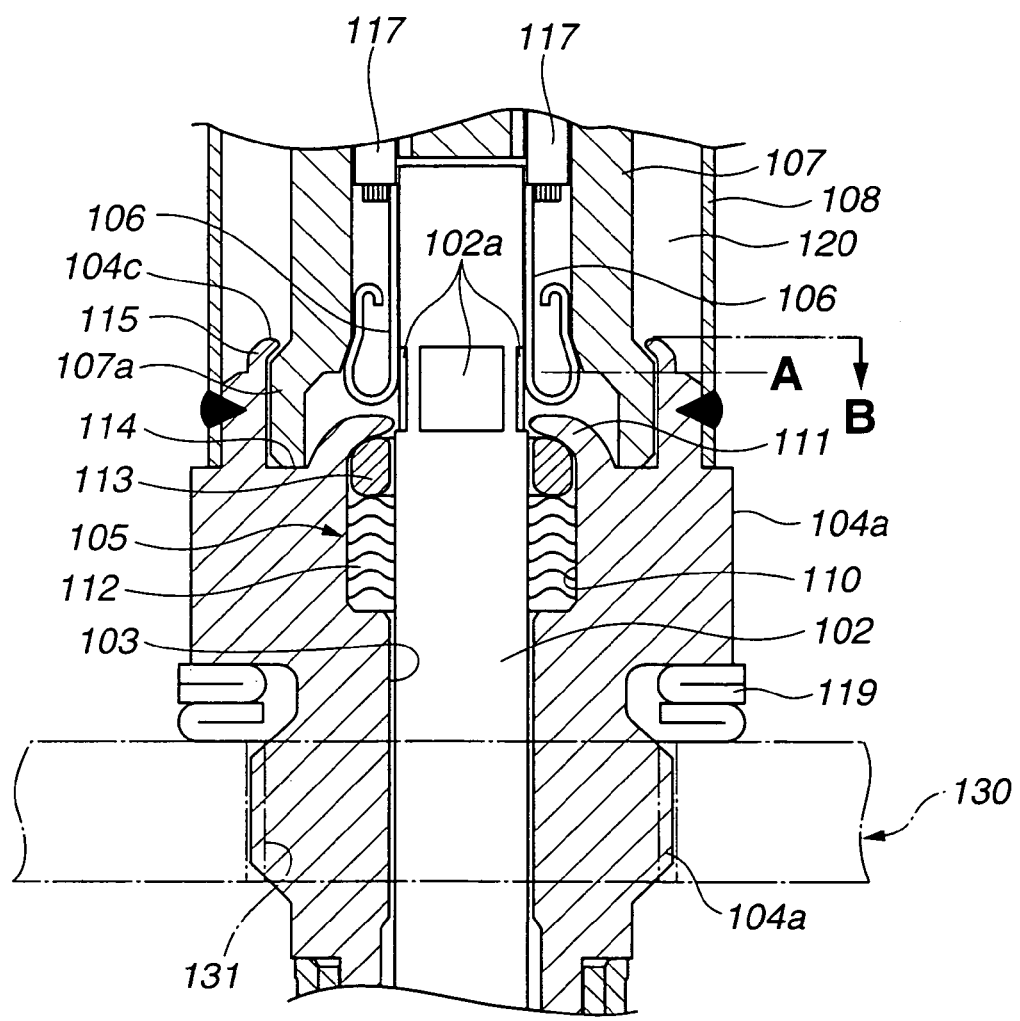
FIG. 4 is a view similar to FIG. 2, showing an oxygen sensor in FIG. 3.

Referring to FIGS. 3 and 4, there is shown second embodiment of the present invention. Referring to FIG. 3, an oxygen sensor 101 comprises a sensor element 102 for sensing an oxygen concentration and converting it to an electric signal, a holder 104 having an element hole 103 through which sensor element 102 is arranged, a sealing positioning portion 105 for sealing a clearance between holder 104 and sensor element 102 and positioning sensor element 102 in holder 104, terminals 106 arranged to be in press contact with respective contacts 102a of sensor element 102 which protrude upward from holder 104 and for taking an output from sensor element 102, a terminal holding insulator 107 secured to holder 104 at a first end and for holding terminals 106, a casing 108 secured to holder 104 at the first end and for covering the outer periphery of terminal holding insulator 107, and a protector 109 secured to holder 104 at a second end and for covering the outer periphery of sensor element 102 protruding from holder 104.

Sensor element 102 is shaped like a cylindrical rod, and includes contacts 102a at the top and an oxygen measuring portion 102b at the bottom.

Holder 104 includes at the top a hexagonal portion 104a presenting a hexagon when viewed from above. By engaging a tool with hexagonal portion 104a, a torque can readily be provided to holder 104. A thread 104b is formed with the outer periphery of the bottom of holder 104. A gasket 119 is interposed between hexagonal portion 104a and thread 104b of holder 104.

Referring to FIG. 4, sealing positioning portion 105 comprises a powder filling space 110 arranged at the overall outer periphery of element hole 103 and a caulking (first caulking) 111 arranged in the vicinity of powder filling space 110. A ceramic powder 112 and a resilient spacer 113 are accommodated in powder filling space 110. Spacer 113 is compressed by caulking 111 having caulked deformation to charge ceramic powder 112 in the compressed state, sealing a clearance between sensor element 102 and holder 104 and positioning sensor element 102 in holder 104. Ceramic powder 112 comprises un-sintered talc, and spacer 113 comprises a washer, for example.

Referring to FIG. 4, holder 104 is secured to terminal holding insulator 107 by arranging an insulator positioning groove 114 at an upper end of holder 104 and a caulking (second caulking) 115 at the outer periphery of insulator positioning groove 114, wherein a first-end-side large-diameter portion 107a of terminal holding insulator 107 is disposed in insulator positioning groove 114, and caulking 115 having caulked deformation is engaged with a step of large-diameter portion 107a.

Terminals 106 are shaped to provide a resiliency, and make contact with contacts 102a of sensor element 102 with the aid of their resiliency. A contact position A of contacts 102a of sensor element 102 and terminals 106 is set below an upper end face or first end face 104c of holder 104, more specifically, below an upper end B of caulking 115.

Referring to FIG. 3, a sealing rubber 116 is arranged inside the top of casing 108, and a plurality of harnesses 117 are led outward therethrough. One ends of harnesses 117 are connected to terminals 106. Casing 108 includes a caulking 108a by which sealing rubber 116 is secured to casing 108 and through which the sealing quality is ensured between sealing rubber 116 and harnesses 117 and between sealing rubber 116 and casing 108.

Casing 108 is shaped cylindrically, and is secured to holder 104 by laser welding, for example, through which the sealing quality is ensured between casing 108 and holder 104. Casing 108 is sufficiently larger in contour than terminal holding insulator 107, which provides a void 120 between casing 108 and terminal holding insulator 107.

Protector 109 is shaped like a bottomed and double-structured cylinder, and has side walls through which small holes 109a for gas circulation are formed. Protector 109 is secured to holder 104 by laser welding, for example. Optionally, other fixing method such as spot welding or caulking can be adopted.

Oxygen sensor 101 is secured to an exhaust pipe 130 by engaging thread 104b of holder 104 in a threaded hole 131 of exhaust pipe 130, and is disposed with its portion covered with protector 109 protruding into exhaust pipe 130. The airtightness between oxygen sensor 101 and exhaust pipe 130 is ensured by gasket 119.

With the structure, when gas circulating through exhaust pipe 130 flows into oxygen sensor 101 through small holes 109a of protector 109, oxygen contained in gas enters oxygen measuring portion 102b of sensor element 102. Then, oxygen measuring portion 102b senses a concentration of oxygen contained in gas and converts it to an electric signal. This electric-signal information is output to the outside through terminals 106 and harnesses 117.

The second embodiment produces substantially the same effects as those of the first embodiment. Particularly, in the second embodiment, the protruding length of sensor element 102 and terminal holding insulator 107 from the upper end of holder 104 can be reduced by the fact that contact position A of sensor element 102 and terminals 106 is set below upper end face 104c of holder 104, resulting in a reduction in overall length L1 as compared with the related art.

Figure 5:
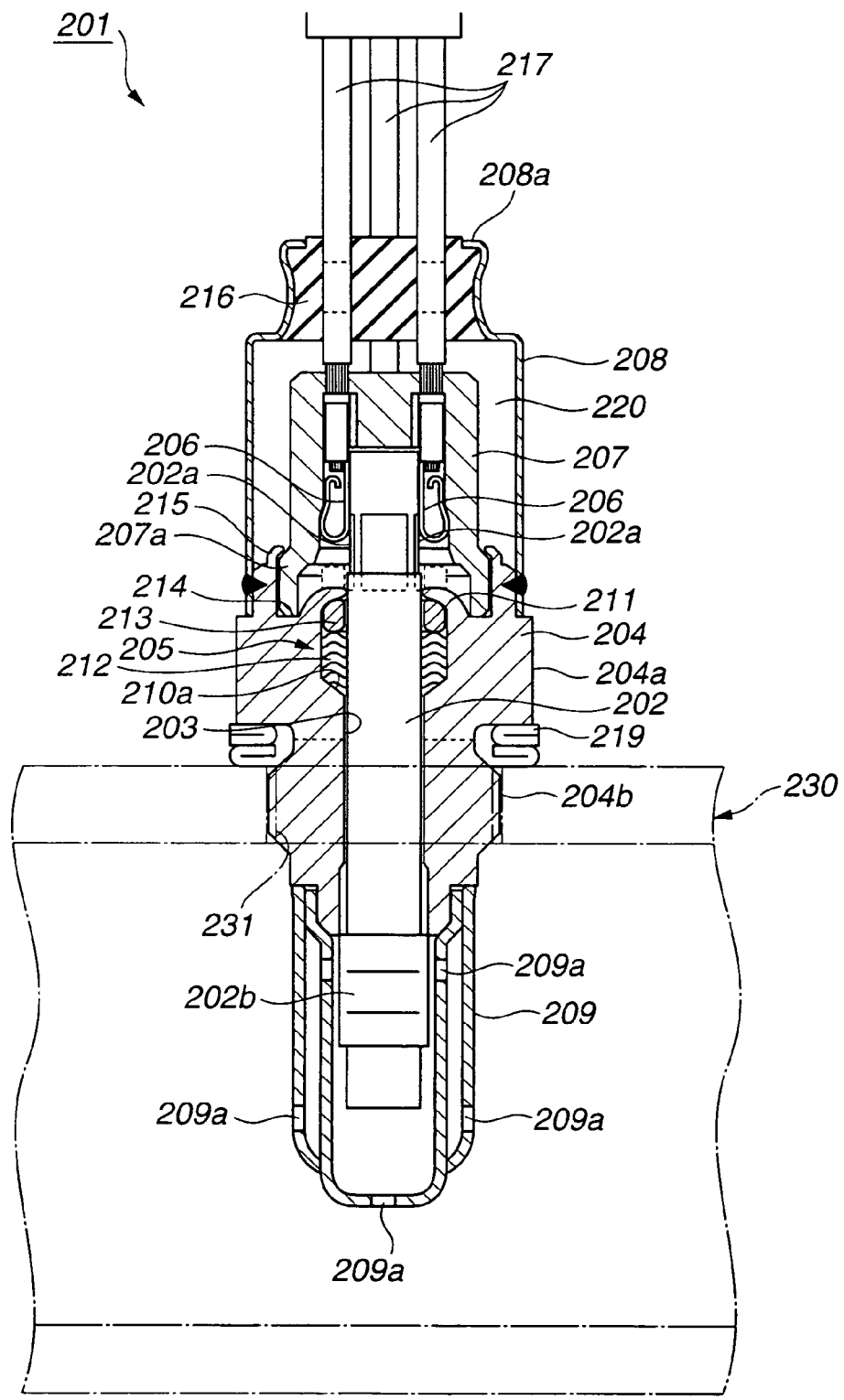
FIG. 5 is a view similar to FIG. 3, showing a third embodiment of the present invention.

Referring to FIGS. 5-7B, there is shown third embodiment of the present invention. Referring to FIG. 5, an oxygen sensor 201 comprises a sensor element 202 for sensing an oxygen concentration and converting it to an electric signal, a holder 204 having an element hole 203 through which sensor element 202 is arranged, a sealing portion 205 for sealing a clearance between holder 204 and sensor element 202 and positioning sensor element 202 in holder 204, terminals 206 arranged to be in press contact with respective contacts 202a of sensor element 202 which protrude upward from holder 204 and for taking an output from sensor element 202, a terminal holding insulator 207 secured to holder 204 at a first end and for holding terminals 206, a casing 208 secured to holder 204 at the first end and for covering the outer periphery of terminal holding insulator 207, and a protector 209 secured to holder 204 at a second end and for covering the outer periphery of sensor element 202 protruding from holder 204.

Sensor element 202 is shaped like a cylindrical rod, and includes contacts 202a at the top and an oxygen measuring portion 202b at the bottom.

Holder 204 includes at the top a hexagonal portion 204a presenting a hexagon when viewed from above. By engaging a tool with hexagonal portion 204a, a torque can readily be provided to holder 204. A thread 204b is formed with the outer periphery of the bottom of holder 204. A gasket 219 is interposed between hexagonal portion 204a and thread 204b of holder 204.

Figure 6:
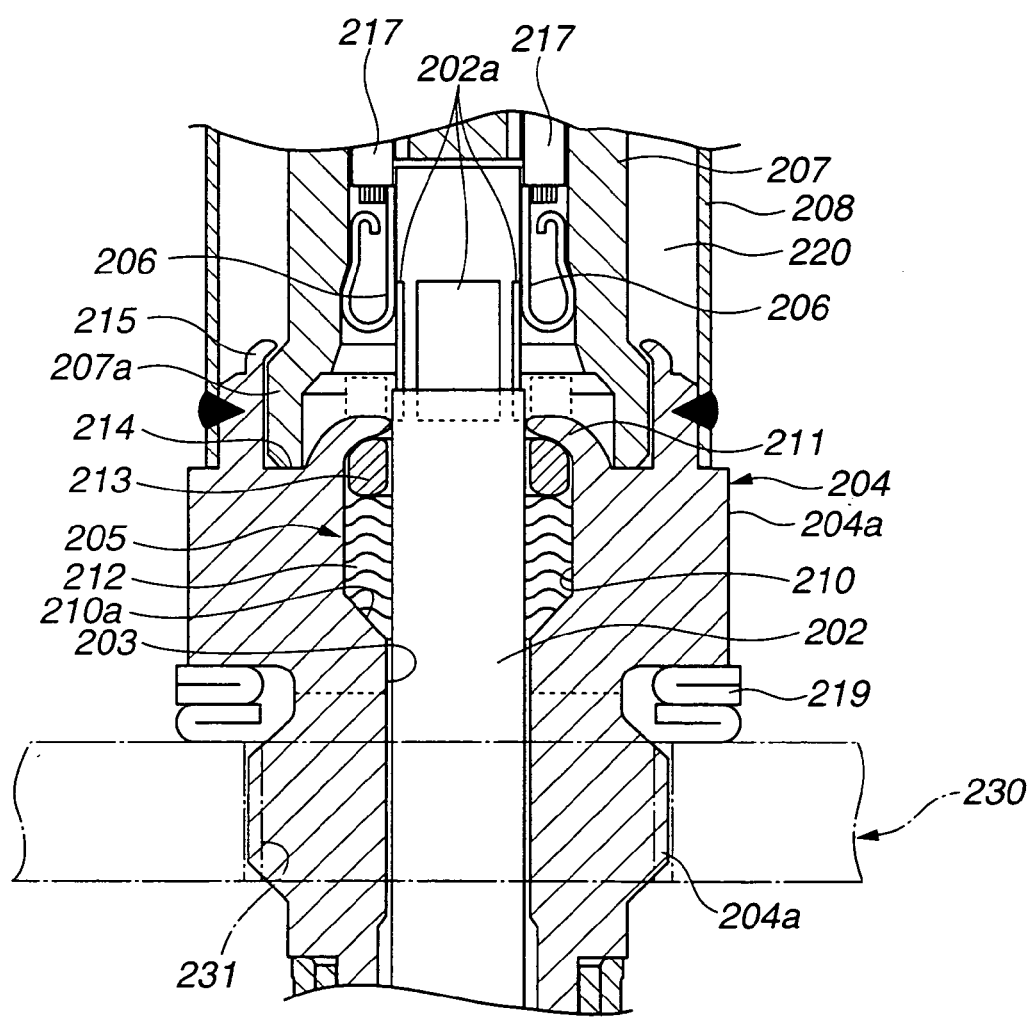
FIG. 6 is a view similar to FIG. 4, showing an oxygen sensor in FIG. 5.
Figure 7A:
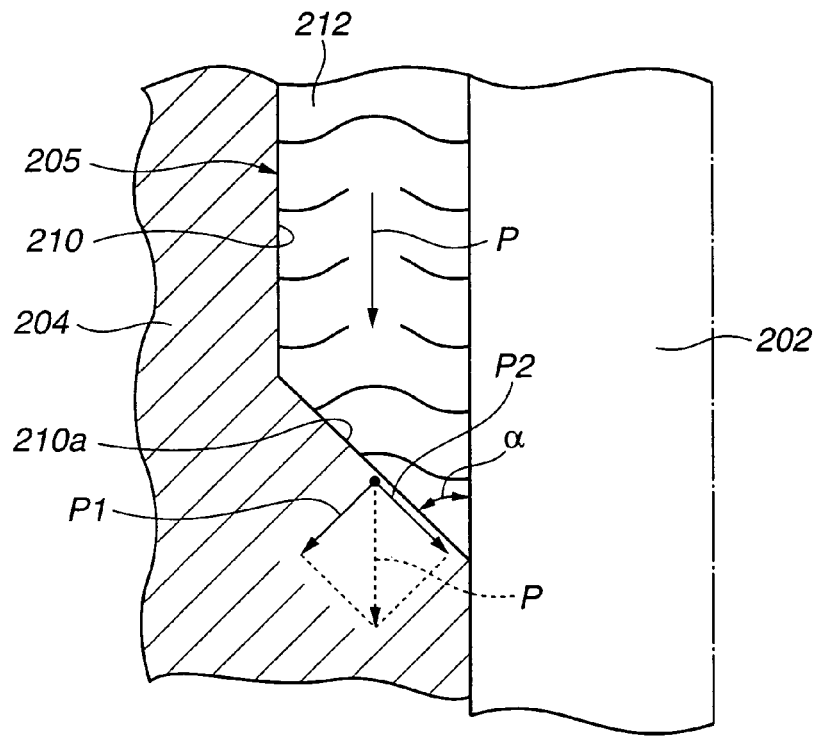
FIG. 7A is a view similar to FIG. 6, for explaining a load acting on the inclined surface of the bottom of a powder filling space.
Figure 7B:
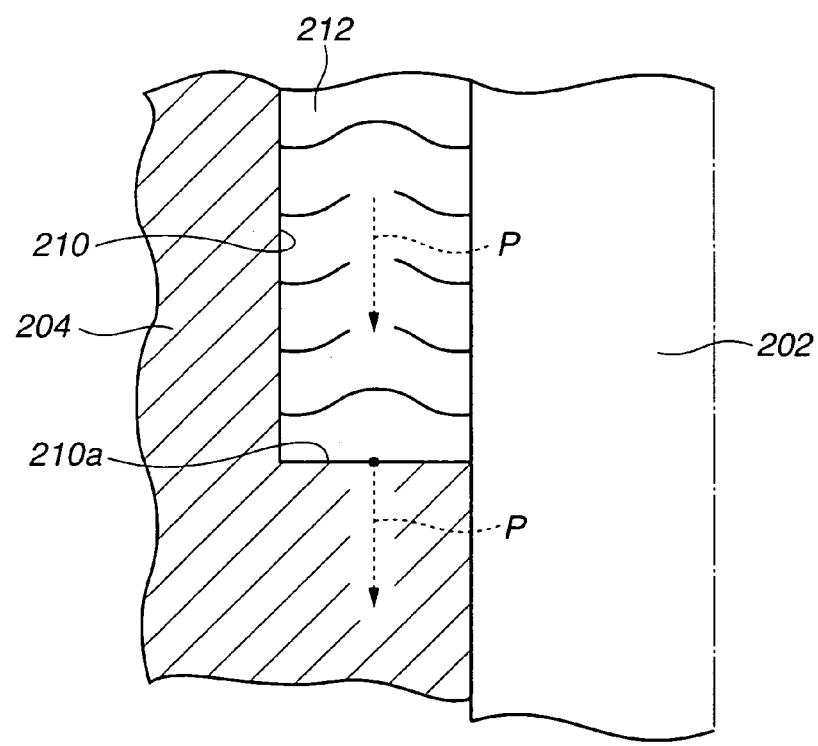
FIG. 7B is a view similar to FIG. 7A, for explaining a load acting on the flat surface of the bottom of the power filling space.

Referring to FIG. 6, sealing portion 205 comprises a powder filling space 210 arranged at the overall outer periphery of element hole 203 and a caulking (second caulking) 211 arranged in the vicinity of powder filling space 210. A ceramic powder 212 and a resilient spacer 213 are accommodated in powder filling space 210. Spacer 213 is compressed by caulking 211 having caulked deformation to charge ceramic powder 212 in the compressed state, sealing a clearance between sensor element 202 and holder 204 and positioning sensor element 202 in holder 204.

The bottom face of powder filling space 210 which undergoes a load of ceramic powder 212 includes an inclined face 210a gradually protruding in the load direction from the outer periphery to the inner periphery. In the third embodiment, referring to FIG. 7A, an angle of inclination a of the inclined face 210a is set at about 45°.

Ceramic powder 212 comprises un-sintered talc, and spacer 213 comprises a washer, for example.

Referring to FIG. 6, holder 204 is secured to terminal holding insulator 207 by arranging an insulator positioning groove 214 at an upper end of holder 204 and a caulking (second caulking) 215 at the outer periphery of insulator positioning groove 214, wherein a first-end-side large-diameter portion 207a of terminal holding insulator 207 is disposed in insulator positioning groove 214, and caulking 215 having caulked deformation is engaged with a step of large-diameter portion 207a.

Terminals 106 are shaped to provide a resiliency, and make contact with contacts 202a of sensor element 202 with the aid of their resiliency. A contact position of contacts 202a of sensor element 202 and terminals 206 is set just above an upper end face of holder 204.

Referring to FIG. 5, a sealing rubber 216 is arranged inside the top of casing 208, and a plurality of harnesses 217 are led outward therethrough. One ends of harnesses 217 are connected to terminals 206. Casing 208 includes a caulking 208a by which sealing rubber 216 is secured to casing 208 and through which the sealing quality is ensured between sealing rubber 216 and harnesses 217 and between sealing rubber 216 and casing 208.

Casing 208 is shaped cylindrically, and is secured to holder 204 by laser welding, for example, through which the sealing quality is ensured between casing 208 and holder 204. Casing 208 is sufficiently larger in contour than terminal holding insulator 207, which provides a void 220 between casing 208 and terminal holding insulator 207.

Protector 209 is shaped like a bottomed and double-structured cylinder, and has side walls through which small holes 209a for gas circulation are formed. Protector 209 is secured to holder 204 by laser welding, for example. Optionally, other fixing method such as spot welding or caulking can be adopted.

Oxygen sensor 201 is secured to an exhaust pipe 230 by engaging thread 204b of holder 204 in a threaded hole 231 of exhaust pipe 230, and is disposed with its portion covered with protector 209 protruding into exhaust pipe 230. The airtightness between oxygen sensor 201 and exhaust pipe 230 is ensured by gasket 219.

With the structure, when gas circulating through exhaust pipe 230 flows into oxygen sensor 201 through small holes 209a of protector 209, oxygen contained in gas enters oxygen measuring portion 202b of sensor element 202. Then, oxygen measuring portion 202b senses a concentration of oxygen contained in gas and converts it to an electric signal. This electric-signal information is output to the outside through terminals 206 and harnesses 217.

The third embodiment produces substantially the same effects as those of the first embodiment. Particularly, in the third embodiment, referring to FIGS. 7A and 7B, the bottom face of powder filling space 210 which undergoes load P of ceramic powder 212 includes inclined face 210a, so that load P acting on holder 204 is distributed by inclined face 210a as shown by arrows in FIG. 7A. This allows an increase in upper limit of load P of ceramic powder 212, resulting in enhanced sealing quality between sensor element 202 and holder 204. In this connection, referring to FIG. 7B, it is noted that, if the bottom face of powder filling space 210 includes a flat face 210b as in the related art, load P of ceramic powder 212 acts axially on holder 201 as a shearing force without being distributed. The third embodiment is designed to distribute load P as described above, and more specifically, divide load P into a component force P1 in the direction perpendicular to inclined face 210a and a component force P2 in the direction along inclined face 210a. Since angle of inclination α is about 45°, component force P1 and component force P2 have roughly the same value.

As described above, according to the present invention, the sensor element can be sealed and positioned in the holder, allowing canceling of the element securing insulator which is required in the related art, resulting in a reduction in number of parts and overall length of the oxygen sensor.

Further, according to the present invention, the ceramic powder is held in the compressed state by a compressive force of the spacer, resulting in secure sealing and positioning of the sensor element.

Still further, according to the present invention, even when the terminal holding insulator undergoes an external force due to pulling of the harnesses or the like, the second caulking can bear this external force, resulting in sure fixing of the terminal holding insulator and the holder.

Still further, according to the present invention, due to rod-like shape of the sensor element, accurate detection of the oxygen concentration can be achieved without being influenced by the orientation of the sensor element, the direction of gas flow, and the like.

Furthermore, according to the present invention, the sensor element and the terminals are externally concealed double with the casing and the terminal holding insulator, and are disposed therein through the void with excellent heat-insulation characteristics, resulting in enhanced durability in the high-temperature environment.

Further, according to the present invention, a contact position of the contacts of the sensor element and the terminals is set above or below the upper end face of the holder, resulting in further reduction in overall length of the oxygen sensor.

Still further, according to the present invention, the bottom face of the powder filling space which undergoes a load of the ceramic powder includes inclined face, so that the load acting on the holder is distributed by the inclined face. This allows an increase in upper limit of the load of the ceramic powder, resulting in enhanced sealing quality between the sensor element and the holder.

Having described the present invention in connection with the illustrative embodiments, it is noted that the present invention is not limited thereto, and various changes and modifications can be made without departing from the scope of the present invention.

By way of example, in the illustrative embodiments, ceramic powder comprises talc. Optionally, ceramic powder may comprise BN and SiN.

The entire teachings of Japanese Patent Application P2003-416473 filed Dec. 15, 2003, Japanese Patent Application P20044-15483 filed Jan. 23, 2004, and Japanese Patent Application P2004-049611 filed Feb. 25, 2004 are hereby incorporated by reference.

What is claimed is:

1. An oxygen sensor, comprising:
   a sensor element which senses an oxygen concentration and convert it to an electric signal;
   a holder having a hole through which the sensor element is arranged;
   a sealing positioning portion which seals a clearance between the sensor element and the holder and positions the sensor element in the holder, the sealing positioning portion being filled with a ceramic powder;
   terminals arranged to be in contact with the sensor element, the terminals taking an output from the sensor element;
   an insulator secured to the holder at a first end, the insulator holding the terminals;
   a casing secured to the holder at the first end, the casing covering an outer periphery of the insulator; and
   a protector secured to the holder at a second end, the protector covering an outer periphery of a portion of the sensor element, the portion protruding from the second end of the holder,
   wherein the sealing positioning portion comprises a space arranged at an overall outer periphery of the hole of the holder and having the ceramic powder charged therein, and a first caulking arranged in a vicinity of the space.

2. The oxygen sensor as claimed in claim 1, further comprising a spacer arranged in the space of the sealing positioning portion,
   wherein the spacer is compressed by the first caulking having caulked deformation to charge the ceramic powder in a compressed state.

3. The oxygen sensor as claimed in claim 1, wherein the space of the sealing positioning portion has a bottom face which undergoes a load of the ceramic powder, the bottom face including an inclined face gradually protruding in a load direction from an outer periphery to an inner periphery of the space.

4. An oxygen sensor, comprising:
   a sensor element which senses an oxygen concentration and convert it to an electric signal;
   a holder having a hole through which the sensor element is arranged;
   a sealing positioning portion which seals a clearance between the sensor element and the holder and positions the sensor element in the holder, the sealing positioning portion being filled with a ceramic powder;

terminals separate from and arranged to be in contact with the sensor element, the terminals taking an output from the sensor element;

an insulator secured to the holder at a first end, the insulator holding the terminals;

a casing secured to the holder at the first end, the casing covering an outer periphery of the insulator; and a protector secured to the holder at a second end, the protector covering an outer periphery of a portion of the sensor element, the portion protruding from the second end of the holder, further comprising:

a groove provided to the holder; and a second caulking arranged at an outer periphery of the groove, wherein a first end of the insulator is disposed in the groove, and the second caulking having caulked deformation is engaged with the insulator, whereby the insulator is secured to the holder.

5. The oxygen sensor as claimed in claim 1, wherein the sensor element is shaped like a rod.

6. The oxygen sensor as claimed in claim 1, wherein the ceramic powder comprises talc.

7. The oxygen sensor as claimed in claim 1, wherein the insulator and the casing cooperate to define a void.

8. The oxygen sensor as claimed in claim 1, wherein a contact position of contacts of the sensor element and the terminals is set above a face of the first end of the holder.

9. The oxygen sensor as claimed in claim 1, wherein a contact position of contacts of the sensor element and the terminals is set below an upper end face of the first end of the holder, as viewed to arrange the first and second ends of the holder in up and down directions.

10. An oxygen sensor, comprising:

a sensor element which senses an oxygen concentration and convert it to an electric signal;

a holder having a hole through which the sensor element is arranged;

a sealing positioning portion which seals a clearance between the sensor element and the holder and positions the sensor element in the holder, the sealing positioning portion being filled with a ceramic powder;

terminals separate from and arranged to be in contact with the sensor element, the terminals taking an output from the sensor element;

an insulator secured to the holder at a first end, the insulator holding the terminals;

a casing secured to the holder at the first end, the casing covering an outer periphery of the insulator; and a protector secured to the holder at a second end, the protector covering an outer periphery of a portion of the sensor element, the portion protruding from the second end of the holder, wherein the insulator has a distal end having a diameter greater than that of a base end, wherein the distal end of the insulator is secured to the holder by caulking.

11. The oxygen sensor as claimed in claim 1, wherein the terminals are located on a distal end of the sensor element.

12. The oxygen sensor as claimed in claim 1, wherein the terminals are in contact with a distal end portion of the sensor element.

13. The oxygen sensor as claimed in claim 1, wherein the terminals are arranged to be in press contact with respective contact portions of the sensor element by means of the holding of the insulator.

14. The oxygen sensor as claimed in claim 1, wherein the terminals are in press contact with respective contact portions of the sensor element by means of a resiliency of the terminals and the holding of the insulator.

15. An oxygen sensor, comprising:

a sensor element which senses an oxygen concentration and convert it to an electric signal;

a holder having a hole through which the sensor element is arranged;

a sealing positioning portion which seals a clearance between the sensor element and the holder and positions the sensor element in the holder, the sealing positioning portion being filled with a ceramic powder, the sealing positioning portion comprising a space arranged at an overall outer periphery of the hole of the holder and having the ceramic powder charged therein, and a first caulking arranged in a vicinity of the space;

terminals arranged to be in contact with the sensor element, the terminals taking an output from the sensor element;

an insulator secured to the holder at a first end, the insulator holding the terminals;

a casing secured to the holder at the first end, the casing covering an outer periphery of the insulator;

a protector secured to the holder at a second end, the protector covering an outer periphery of a portion of the sensor element, the portion protruding from the second end of the holder;

a spacer arranged in the space of the sealing positioning portion;

a groove provided to the holder; and a second caulking arranged at an outer periphery of the groove, wherein the spacer is compressed by the first caulking having caulked deformation to charge the ceramic powder in a compressed state, wherein a first end of the insulator is disposed in the groove, and the second caulking having caulked deformation is engaged with the insulator, whereby the insulator is secured to the holder.

* * * * *